United States Patent [19]

Heuckeroth et al.

[11] Patent Number: 5,082,967
[45] Date of Patent: Jan. 21, 1992

[54] NOVEL FATTY ACID ANALOG ENZYME SUBSTRATES

[75] Inventors: Robert O. Heuckeroth, St. Louis; Steven P. Adams, St. Charles; Jeffrey I. Gordon, St. Louis, all of Mo.; George W. Gokel, Miami, Fla.

[73] Assignee: Washington University, St. Louis, Mo.

[21] Appl. No.: 478,298

[22] Filed: Feb. 9, 1990

Related U.S. Application Data

[63] Continuation-in-part of Ser. No. 208,192, Jun. 16, 1988, and a continuation-in-part of Ser. No. 402,094, Sep. 1, 1989.

[51] Int. Cl.$^5$ .................. C08H 3/00; C07C 321/00; C07C 315/00
[52] U.S. Cl. .................. 562/512; 260/399; 260/405.5; 260/410; 260/413; 560/152; 560/183; 560/186; 562/581
[58] Field of Search .......... 562/512, 587, 581; 586/587; 260/413, 399, 405.5, 410; 560/152, 183, 186

[56] References Cited

U.S. PATENT DOCUMENTS

| | | | |
|---|---|---|---|
| 3,654,326 | 4/1972 | Rosenberger | 260/413 |
| 4,625,057 | 11/1986 | Springmann | 562/588 |
| 4,740,588 | 4/1988 | Adams et al. | 530/328 |
| 4,778,877 | 10/1988 | Adams et al. | 530/328 |
| 4,778,878 | 10/1988 | Adams et al. | 530/328 |

OTHER PUBLICATIONS

Towler and Glaser, Biochemistry 25, 878-884 (1986).
Towler and Glaser, Proc. Natl. Acad. Sci U.S.A. 83, 2812-2816 (1986).
Towler et al., Ibid. 84, 2708-2712 (1987).
Towler et al., J. Biol Chem. 262, 1030-1036 (1987).
Towler et al., Ann. Rev. Biochem., 57, 69-99, (1988).
Heuckeroth et al., Proc. Nat'l. Acad. Sci. U.S.A. 85, 8795-8799 (1988).
Heuckeroth et al., Ibid. 86, 2562-5266 (1989).
The Merck Index, Tenth Ed., 1983, p. ONR-96.
Pascal and Ziering, J. Lipid Res. 27, 221-224 (1986).
Heuckeroth et al., J. Biol. Chem. 263(5), 2127-2133 (1988).
Aleynikov et al., Kolsk Branch of the USSR Acedemy of Sciences, May 3, 1961.
Belov et al., Zhokh, vol. 1, No. 4, D. I. Mendeleev, Chem. Engineering Institute in Moscow, Apr. 18, 1964.

Primary Examiner—Jose G. Dees
Assistant Examiner—Keith MacMillen
Attorney, Agent, or Firm—Scott J. Meyer; James W. Williams, Jr.

[57] ABSTRACT

Novel diheteroatom-substituted fatty acid analog substrates of myristoylating enzymes are provided which contain oxyen and/or sulfur in place of two methylene groups in carbon positions from 3 to 13 in the fatty acid chain of a $C_{13}$-$C_{14}$ fatty acid analog or alkyl ester thereof in which said oxygen or sulfur atoms are separated by at least one methylene group.

14 Claims, No Drawings

NOVEL FATTY ACID ANALOG ENZYME SUBSTRATES

CROSS-REFERENCE TO RELATED APPLICATION

This is a continuation-in-part of copending application Ser. No. 07/208,192, filed June 16, 1988 and application Ser. No. 07/402,094, filed Sept. 1, 1989.

BACKGROUND OF THE INVENTION

This invention relates to novel fatty acid analog substrates of myristoylating enzymes and, more particularly, to diheteroatom-substituted fatty acid analogs in which the heteroatoms are oxygen and/or sulfur and which are useful in the fatty acid acylation of peptides and proteins.

Fatty acid acylation of specific eukaryotic proteins is a well established process which can conveniently be divided into two categories. On the one hand, palmitate ($C_{16}$) is linked to membrane proteins via ester or thioester linkage post-translationally.

On the other hand, it is known that myristate ($C_{14}$) becomes covalently bound to soluble and membrane proteins via amide linkage early in the protein biosynthetic pathway. In the N-myristoylated proteins, amino-terminal glycine residues are known to be the site of acylation.

A variety of viral and cellular proteins have been shown to be thus modified by the covalent attachment of myristate linked through an amide bound to glycine at their amino termini. An example of a most thoroughly studied myristoylated protein is the transforming protein of Rous sarcoma virus, $p60^{v-src}$.

The myristoylation reaction can be represented as follows:

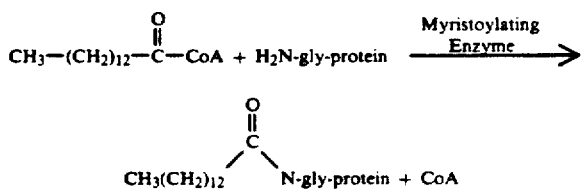

Further background information on the above protein fatty acid acylation can be had by reference to the following series of articles by scientists associated with the Washington University School of Medicine:

Towler and Glaser, *Biochemistry* 25, 878–84 (1986);
Towler and Glaser, *Proc. Natl. Acad. Sci. USA* 83, 2812–2816 (1986);
Towler et al., *Proc. Natl. Acad. Sci. USA* 84, 2708–2712 (1987);
Towler et al., *J. Biol. Chem.* 262, 1030–1036 (1987);
Towler et al., *Ann. Rev. Biochem.* 57, 69–99 (198 );
Heuckeroth et al., *Proc. Natl. Acad. Sci. USA* 85, 8795–8799 (1988); and
Heuckeroth and Gordon, *Proc. Natl. Acad. Sci. USA* 86, 5262–5266 (1989).

Unique synthetic peptides having relatively short amino acid sequencer which are useful as substrates of myristoylating enzymes are described in U.S. Pat. Nos. 4,740,588 and 4,778,878. Examples of such peptides are
Gly-Asn-Ala-Ala-Ala-Ala-Arg-Arg and
Gly-Asn-Ala-Ala-Ser-Tyr-Arg-Arg.

Certain other unique synthetic peptides are inhibits of myristoylating enzymes as described in U.S. Pat. Nos. 4,709,012 and 4,778,877.

BRIEF DESCRIPTION OF THE INVENTION

In accordance with the present invention, novel fatty acid analog substrates for myristoylating enzymes are provided. These novel compounds are diheteroatom-substituted fatty acid analogs in which the heteroatoms are oxygen and/or sulfur and which are useful in the fatty acid acylation of proteins. They contain two atoms of oxygen and/or sulfur in place of two methylene ($-CH_2-$) groups in carbon positions from 3 to 13 in the fatty acid chain of a $C_{13}-C_{14}$ fatty acid or alkyl ester thereof. The carboxyl carbon atom is defined herein as number 1 based on conventional nomenclature. The heteroatoms are preferably separated by about 2 to 5 methylene groups in these fatty acid analogs. Preferred alkyl esters of the fatty acid analogs have from 1 to 6 carbon atoms in the alkyl group.

These novel substrate compounds are useful for studying the regulation of enzyme action in fatty acid acylation and the role of N-myristoylation in protein function. They can serve as synthetic substrates for the N-myristoylating enzymes in sources such as yeasts, fungi, wheat germ lysates and mammmalian cells. These novel compounds differ in hydrophobicity from myristic acid while maintaining approximately the same chain length. Thus, when incorporated into myristoyl-proteins, they should alter the acylprotein's subsequent interactions with membranes or with other proteins. They also have potential use as antiviral, antifungal and antineoplastic agents.

Illustrative examples of the novel diheteroatom-substituted fatty acid analog substrate compounds of this invention are:

A. 6,12-Dithiatetradecanoic acid

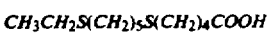

B. 6,12-Dioxatetradecanoic acid

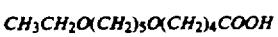

C. 7,10-Dithiatetradecanoic acid

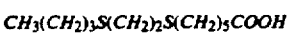

D. 7,10-Dioxatetradecanoic acid

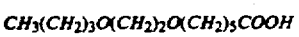

E. 9,12-Dioxatetradecanoic acid

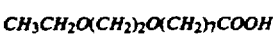

F. 9,12-Dithiatetradecanoic acid

G. 9-Oxa,12-thiatetradecanoic acid

H. 12-Oxa,9-thiatetradecanoic acid

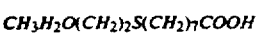

I. 10,13-Dioxatetradecanoic acid

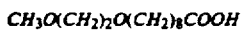

J. 12-Oxa,6-thiatetradecanoic acid

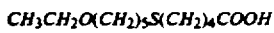

These type compounds alternatively can be named by their common fatty acid derivation, e.g. designated as 6,12-dithiamyristic acid.

DETAILED DESCRIPTION OF THE INVENTION

The preparation of many of the diheteroatom-substituted fatty acid analog substrate compounds can be carried out by methods analogous to the preparation of mixed ethers by the Williamson synthesis. Thus, an appropriate ω-bromocarboxylic acid can be reacted with an alkoxy alcholate to produce the dioxy-substituted fatty acid ether. So also, an appropriate ω-iodocarboxylate ester can be reacted with an alkylthioalkyl thiol followed by alkaline cleavage of the ester group to produce the dithia-substituted fatty acid ether.

Both of the foregoing type reactions preferably are carried out in organic solvent medium at refluxing temperatures until the desired reaction is essentially complete.

Illustratively, 2-butoxyethanol can be reacted with sodium hydride and the resulting alcoholate reacted with 6-bromohexanoic acid to give 7,10-dioxatetradecanoic acid. So also, 2-ethoxyethanol can be reacted with sodium hydride and the resulting alcoholate reacted with 8-bromooctanoic acid to provide 9,12-dioxatetradecanoic acid.

To illustrate the preparation of the dithia-substituted fatty acid ethers, 5-ethylthiopentane thiol can be reacted with sodium hydride and the resulting product reacted with ethyl 5-iodovalerate to yield ethyl 6,12-dithiatetradecanoate. The ester group can then be removed by treatment with alkali metal hydroxide, e.g. NaOH, to produce the desired 6,12-dithiatetradecanoic acid.

Similarly, other dithia- or dioxy-substituted fatty acid ethers can be made in an analogous manner by selecting appropriate alkyl and fatty acid chain lengths in the reactant compounds to give the desired products.

In the case of the preparation of one of the diheteroatom-substituted fatty acid analogs, namely 6,12-dioxatetradecanoic acid, considerable difficulties were encountered. Thus, the reaction of 5-ethoxypentan-1-ol with a variety of 5-halovalerate alkyl esters afforded ester exchange products rather than the desired products of Williamson ether synthesis. Accordingly, a novel synthesis of the 6,12-dioxatetradecanoic acid was developed as described in Example 5, below. This synthesis can be summarized as follows:

Commercially available 1,5-pentanediol was monoethylated (2, 71%) using an equivalent of iodoethane and NaH in THF. The diol was also converted into its mono-tetrahydropyranyl ether (4, 54%) by treatment with dihydropyran and toluenesulfonic acid in methylene chloride [Ngooi et al., J. Org. Chem. 54, 911 (1989)]. Ethoxyalcohol 2 was tosylated (pyridine, TsCl, 0° C.) in 40% yield to afford oily 3. The low yield reflects the need to distill this reactive ether. Tosylate 3 was then allowed to react with mono-THP alcohol 4 (NaH, THF, reflux, 24h) to afford, after deprotection, [Corey et al., J. Am. Chem. Soc. 91, 4318 (1969), the diether alcohol, 6, in 37% yield. Oxidation using Kiliani reagent (Na2Cr2O7—2H2O/H2SO4/H2O) [Kiliani and Merk, Chem. Ber. 34 3562 (1901)] afforded 6,12-dioxatetradecanoic acid, 1, in 52% yield as a colorless oil.

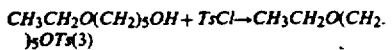

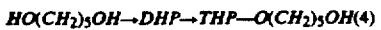

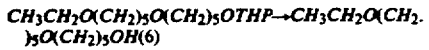

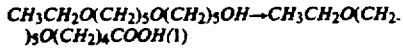

Although specific methods of preparation of the novel diheteroatom-substituted fatty acid analogs are described herein, it will be understood that the novel compounds of this invention are not limited to any specific method of preparation.

The novel diheteroatom-substituted fatty acid analog compounds of the invention were analyzed in a conventional in vitro yeast N-myristoyltransferase (NMT) assay as published by Heuckeroth et al., Proc. Nat'l. Acsd. Sci. USA 85, 8795-8799 (1988). In this assay, the test compounds are first converted to their respective fatty acyl CoA derivatives and then tested as substrates for the yeast NMT. In these assays, the reduction in hydrophobicity observed with, respectively, two sulfurs or two oxygens, or one sulfur and one oxygen, for methylene substitutions is generally about twice that observed with a single sulfur or oxygen substitution. Although the diheteroatom-substituted fatty acid analogs are active substrates of the myristoylation reaction, kinetic analysis of these compounds indicated that they are less effective than the single sulfur or oxygen substituted analogs by such analysis. Thus, the peptide $K_m$ with 6,12-dithiamyristoyl CoA is 4.4-fold higher than with myristoyl CoA, while the peptide $K_m$s with the double oxygen substituted analogs are 7.5 to 12-fold higher. However when the velocities are considered, the double sulfur-substituted analog appears to produce only a 2-fold reduction in peptide catalytic efficiency ($V_m/K_m$) while 7,10- and 9,12-dioxamyristoyl CoAs are associated with 5- and 10-fold decreases in peptide catalytic efficiency, respectively.

The effective use of the diheteroatom-substituted fatty acid analogs of this invention as substrates of the myristoylation reaction is evident by comparison with a triheteroatom-substituted fatty acid analog, namely 6,9,12-trioxatetradecanoic acid, which exhibited virtually no activity even at a concentration of 100 μM.

The following examples will further illustrate the invention although it will be appreciated that the invention is not limited to these specific examples.

In these examples, the following procedures were used: ¹H NMR were recorded on a Hitachi Perkin-Elmer R-600 spectrometer or on a Varian VXR 400 spectrometer in CDCl3 containing 1% Me4Si. Data are reported in the following order: chemical shift, spin multiplicity (b=broad, s=singlet, d=doublet, t=triplet, q=quartet, m=multiplet), integration, and coupling constant. Infrared spectra were recorded on a Perkin- Elmer 599 infrared spectrometer. All commercially available reagents were used without further purification. Column chromatography was carried out with EM Science Al$_2$O$_3$(80–230 mesh) and Merck Kieselgel 60 (70–230 mesh). Precoated sheets (aluminum oxide 60F$_{254}$ neutral Type E or silica gel 60F$_{254}$, 0.2 mm thick) were used for TLC analysis. Combustion analyses were conducted by Atlantic Microlab. Inc., Atlanta, GA.

EXAMPLE 1

Ethyl 6,12-dithiatetradecanoate

NaH (0.4 g, 8.4 mmol) was washed with hexanes and then suspended in dry THF (55 mL). 5-Ethylthiopentanethiol (8 mmol, 73% pure by GC analysis, contaminated by 1,5-bis(ethylthio)pentane, 1.80 g of mixture) in THF (8 mL) was added and stirred for 1 h at room temperature. Ethyl 5-iodovalerate (2.1 g, 8 mmol) in THF (8 mL) was added and the mixture refluxed for 8 h. The solvent was evaporated in vacuo, the residue was dissolved in EtOAc (150 mL), washed with water (2 ×50 mL), brine (50 mL), dried (Na$_2$SO$_4$), chromatographed (silica gel, EtOAc/hexanes 1:10) and distilled (Kugelrohr) to yield the title compound (1.86 g, 80%) as a colorless oil (bp 147° C.–149° C./0.2 torr). IR (neat): 1740 cm$^{-1}$. $^1$H-NMR: 1.25 (t, 6H); 1.50 (quintet, 2H); 1.54–1.67 (m, 6H); 1.73 quintet, 2H); 2.32 (t, 2H); 2.46–2.57 (m, 8H); and 4.12 (q, 2H). Anal. Calcd for C$_{14}$H$_{28}$S$_2$O$_2$: C, 57.49; H, 9.65%. Found: C, 57.36; H, 9.59%.

EXAMPLE 2

6,12-Dithiatetradecanoic acid

Sodium hydroxide (1 M, 6.2 mL, 6.2 mmol) was added to a solution of ethyl 6,12-dithiatetradecanoate (0.9 g, 3.1 mmol) in MeOH (15 mL). After stirring for 4 hours, water (20 mL) was added and the reaction mixture was acidified (pH 1, HCl) extracted with EtOAc (2×100 mL), and the organic phase was washed with water (20 mL), brine (20 mL), and then dried (Na$_2$SO$_4$). The product crystallized from n-hexane to yield the title compound as a white solid (0.77 g, 95%, mp 49.5° C.–50.0° C.). IR: 3000, 1720 cm$^{-1}$; $^1$H NMR, 1.23 (t, 3H), 1.49 (quintet, 2H), 1.56–1.68 (m, 6H), 1.74 (quintet, 2H), 2.38 (t, 2H), 2.51 (t, 2H), 2.53 (t, 4H), 2.54 (q, 2H), and 10.45 (b, 1H). Anal. Calcd for C$_{12}$H$_{24}$S$_2$O$_2$: C, 54.50; H, 9.15%. Found: C, 54.59; H, 9.21%.

EXAMPLE 3

7,10-Dioxatetradecanoic acid

NaH (2.2 g, 0.045 mol) was allowed to react with 2-butoxyethanol (50 mL) during 1 h. 6-Bromohexanoic acid (4.2 g, 0.0215 mol) was added, the mixture was heated at reflux for 24 h, cooled, and the solvent was removed in vacuo. The residue was dissolved in ether (50 mL), washed with water (3×40 mL), the aqueous phase was acidified (pH 1.0, 6 M HCl), washed with ether, and the solvent removed in vacuo. The yellow oil was chromatographed (silica gel, 10%–30% Et$_2$O/CH$_2$Cl$_2$) and distilled (Kugelrohr) to yield the title product (2.0 g, 50%, bp 120° C./0.02 torr). IR: 1740 cm$^{-1}$. $^1$H NMR: 0.98 (t, 3H), 1.4 (m, 4H) 1.6 (m, 6H), 2.4 (t, 2H), 3.4 (t, 4H), 3.6 (s, 4H). Anal. Calcd for C$_{12}$H$_{24}$O$_4$: C, 62.04; H, 10.41%. Found C, 61.99; H, 10.47%

EXAMPLE 4

9,12-Dioxatetradecanoic acid

NaH (2.4 g, 0.05 mol) was allowed to react with 2-ethoxyethanol (50 mL) during 30 min. 8-Bromooctanoic acid (4.8 g, 0.021 mol) was added, the solution heated at reflux for 24 h, cooled, and the solvent removed in vacuo. The residue was dissolved in ether, washed with water, the aqueous phase acidified (pH 1, HCl), and washed again with ether. The organic phase was dried (MgSO$_4$), the solvent removed in vacuo, and the residue chromatographed (silica gel, 10%–25% Et$_2$O/CH$_2$Cl$_2$), and distilled (Kugelrohr) to afford the title compound (0.4 g, 8%) as a yellow oil (bp 232° C./0.02 torr). IR: 1750 cm$^{-1}$: $^1$H NMR: 1.3 (t, 3H); 1.35 (bs, 6H); 1.6 (m, 4H); 3.5 (m, 8H). Anal. Calcd for C$_{12}$H$_{24}$O$_4$: C, 62.07; H, 10.41%. Found: C, 61.95; H, 10.46%.

EXAMPLE 5

A

5-Ethoxypentan-1-ol (2)

NaH (4.2 g, 0.11 mol) was washed with hexane and then suspended in dry THF (400 mL). Pentane-1,5-diol (10.4 g, 0.1 mol) in THF (50 mL) was added and stirred for 1 h at room temperature. Iodoethane (17.2 g, 0.11 mol) in THF (50 mL) was added and the mixture was refluxed for 48 h. After evaporation of the solvent, the residue was dissolved in EtOAc (300 mL). The organic phase was washed with water (2×50 mL), brine (50 mL), and dried (Na$_2$SO$_4$). The residue was purified by column chromatography on alumina with 10% 2-propanol in hexane, and then Kugelrohr distillation to give the title product (2) (9.4 g, 71%); bp 45° C.–46° C./0.005 torr; IR(neat): 3400 (broad) and 1115 cm$^{-1}$; $^1$H NMR: 1.22 (t, 3H, J=6.8 Hz), 1.42 (m, 2H), 1.56 (m, 4H), 3.43 (t, 4H, J=5.8 Hz), 3.48 (q, 2H, J=6.8 Hz), and 3.58 ppm (b s, 1H).

B Synthesis of 6,12-dioxamyristic acid.

5-Oxaoctyl p-toluenesulfonate (3)

Compound (2) (3.3 g, 0.025 mol) was dissolved in pyridine (25 mL) and then cooled to 0° C. To this solution was added p-toluenesulfonyl chloride (5.7 g, 0.03 mol) with vigorous stirring. After 2h, the reaction mixture was stirred at room temperature for another 5 h, and then poured into ice. The aqueous solution was extracted with EtOAc (150 mL). The organic phase was washed with water (50 mL), brine (50 mL), and dried (Na$_2$SO$_4$). The residual oil was purified by Kugelrohr distillation to give the title product (3) (3 g, 40%); bp 128° C.–134° C./0.08 torr, IR(neat): 1355 and 1180 cm$^{-1}$; $^1$H NMR: 1.17 (t, 3H, J=7 Hz), 1.3–1.8 (m, 6H), 2.43 (s, 3H), 3.36 (t, 2H, J=7 Hz), 3.42 (q, 2H, J=7 Hz), 4.0 (t, 2H, J=6 Hz), 7.28 (d, 2H, J =8Hz), and 7.76 ppm (d, 2H, J=6 HE).

C

5-(Tetrahydropyranyl)oxypentan-1-ol (4)

To a mixture of pentane-1,5-diol(5.2 g, 0.05 mol) and p-toluenesulfonic acid (0.1 g, 0.53 mmol) in CH$_2$Cl$_2$ (120 mL) was added slowly dihydro-2H-pyran (4.6 g, 0.055 mol) in CH$_2$Cl$_2$ (30 mL) at 0° C. After stirring for 2 h at 0° C. and for another 1 h at room temperature, saturated NaHCO$_3$ (50 mL) was added to the reaction mixture. The CH$_2$Cl$_2$ layer was washed with saturated NaHCO$_3$ (50 mL), water (50 mL), and dried (MgSO$_4$). The residue was purified by column chromatography on silica gel with EtOAc:hexane (1:1, v/v) and subsequent Kugelrohr distillation to give the title product (4, 5.1 g, 54%); bp 80° C.-85° C./0.1 torr; IR(neat): 3450 (broad) and 1135 cm$^{-1}$; $^1$H NMR: 1.3-1.9 (m, 12H), 2.4 (b s, 1H), 3.3-3.9 (m, 6H), and 4.58 ppm (m, 1H).

D 6,12-Dioxatetradecane-1-ol (6)

The reaction of compound 3 (2.86 g, 0.01 mol) and compound 4 (1.88 g, 0.01 mol) in the presence of NaH (0.4 g, 0.011 mol) in dry THF (70 mL) was carried out in the same manner as described above. The crude oil was chromatographed on silica gel to give a mixture (2.4 g) of the starting material (3) and compound (5) (40:60). To this mixture in MeOH (50 mL) was added p-toluenesulfonic acid (28 mg), and the reaction mixture was stirred for 3 h at room temperature. After evaporation of the solvent, the residue was dissolved in EtOAc (150 mL). The organic phase was washed with 5% NaHCO$_3$ (2×50 mL), water (50 mL), brine (50 mL) and dried (Na$_2$SO$_4$). The residue was purified by column chromatography on silica gel with EtOAc:hexane (1:1) and Kugelrohr distillation to give the title product (6, 0.8 g, total yield 37%); bp 88° C.-92° C./0.05 torr; IR(neat): 3460 (broad) and 1115 cm$^{-1}$; $^1$H NMR: 1.18 (t, 3H, J=7 Hz), 1.3-1.8 (m, 12H), 2.1 (b s, 1H), 3.38 (t, 8H J=6.5 Hz), and 3.43 ppm (q, 2H, J=7 Hz).

E 6,12-Dioxatetradecanoic acid (1)

Kiliani reagent [*Chem. Ber.* 34, 3562 (1901)] was prepared in situ by dissolving Na$_2$Cr$_2$O$_7$ 2H$_2$O (3 g) in a cold solution of H$_2$SO$_4$ (4 g) and water (13.5 g). To a solution of compound 6 (1.2 g, 5.5 mmol) in AcOH (28 mL) was added Kiliani reagent (20 g) at 0° C. The reaction mixture was stirred for 7 h at room temperature. Water (120 mL) was added to the mixture and then extracted with EtOAc (2×100 mL). The organic phase was washed with water (2×30 mL) and dried (Na$_2$SO$_4$). The residual oil was purified by column chromatography on silica gel with CHCl$_3$:MeOH (7:1) and subsequent Kugelrohr distillation to give the title product (1) (0.7 g, 52%); bp 128° C.-132 ° C./0.1 torr); IR(neat): 3000 (broad) and 1730 cm$^{-1}$; $^1$H NMR: 1.23 (t, 3H, J=7.4 Hz), 1.3-1.8 (m, 10H), 2.38 (t, 2H, J=5.4 Hz), 3.3-3.6 (m 8H), and 9.98 ppm (b s, 1H); Anal. Calcd for C$_{12}$H$_{24}$O$_4$: C, 62.04; H, 10.41%. Found: C, 61.95; H, 10.43%.

EXAMPLE 6

10,13-Dioxatetradecanoic acid

A mixture of 2-methoxyethanol (0.8 mL, 10 mmole), t-butyl-9-bromononanoate (1 g, 3.4 mmoles) and tetrabutylammonium hydrogen sulfate (0.25 g, 0.34 mmoles) in 50% sodium hydroxide (4 mL) and toluene (2 mL) was stirred vigorously at room temperature for 3 h. The reaction mixture was poured into cold water (20 mL) and products were extracted into ethyl acetate (25 mL). The organic phase was washed with water (3 ×15 mL), dried (Na$_2$SO$_4$) and concentrated under reduced pressure to give an oily residue which was purified by flash chromatography using EtOAc-Hexane (1:9, v/v) to afford the desired ester (0.4 g, 58%) and unreacted t-butyl bromoester (0.3 g): $^1$H NMR δ3.56 (m, 4, —OCH$_2$), 3.45 , 2,—OCH$_2$), 3.39 (s, 3, —OCH$_3$), 2.19 (t, 2, —CH$_2$), 1.56 (m, 4, —CH$_2$), 1.44 (s, 9,-t-butyl), 1.3 (m, 8, —CH$_2$); FAB MS, m/z 295 (M+Li) and 239. This material (0.32 g) was converted to the corresponding carboxylic acid by heating with trifluoroacetic acid (0.3 mL) in THF (3 mL) at 55° C. for 4 h. After removal of the solvent under reduced pressure the residue was purified by flash chromatography using EtOAc-hexane (2:8, v/v) to give 10,13-dioxatetradecanoic acid as a colorless oil: $^1$H NMR δ: 3.57 (m, 4—OCH$_2$), 3.45 (t, 2, —OCH$_2$), 3.39 (s, 3, —OCH$_3$), 2.34 (t, 2, —OCH$_2$), 1.6 (m, 4, —CH$_2$), 1.3 (m, 8, —CH$_2$); FAB MS, m/z 239 (M+Li); High-resolution FAB MS, m/z 239.1854 (M+Li) requires 239.1839.

EXAMPLE 7

9-Oxa-12-thiatetradecanoic Acid

NaH (1.85 g, 0.046 mol) was washed with hexane and then suspended in dry THF (60 mL). 3-Thiapentane-1-ol (4.67 g, 0.04 mol) in THF (20 mL) was added and stirred for 1 h at room temperature. 1,6-Dibromohexane (9.76 g, 0.04 mol) in THF (20 mL) was added and the mixture was refluxed for 20 h. After evaporation of the solvent, the residue was dissolved in ethyl acetetate (200 mL). The organic phase was washed with water (2×50 mL), and dried (Na$_2$SO$_4$). The crude product was purified by Kugelrohr distillation to give 7-oxa-10-thiadodecyl bromide (3.34 g, 31%); bp 48° C. -56° C./0.04 torr; NMR: 1.25 (3H, t, J=7 Hz), 1.2-1.9 (8H, m), 2.59 (2H, q, J=7 Hz), 2.68 (2H, t, J=7 Hz), and 3.2-3.7 ppm (6H, m).

Sodium metal (0.31 g, 0.014 mol) was dissolved in absolute EtOH (20 mL). To this mixture was added diethyl malonate (2.2 g, 0.014 mol) in EtOH (5 mL) and the above 7-oxa-10-thiadodecyl bromide (3 g, 0.011 mol) in EtOH (5 mL) at room temperature. The reaction mixture was refluxed for 5 h. After evaporation of the solvent, the residue was dissolved in ethyl acetate (120 mL). The organic phase was washed with water (2×30 mL), brine (30 mL), and dried (Na$_2$SO$_4$). The crude product was purified by Kugelrohr distillation to give ethyl- 2-ethoxycarbonyl9-oxa-12-thiatetradecanoate (2.3 g, 58%); bp 122° C.-128° C./0.04 torr; NMR: 1.27 (6H, t, J=7 Hz), 3.3-3.7 (5H, m), and 4.17 ppm (4H, q, J=7 Hz), 1.2-1.9 (10H, m), 2.59 (2H, q, J=7 Hz), 2.68 (2H, t, J=7 Hz), 3.1-3.7 (5H, m), and 4.17 ppm (4H, q, J=7 Hz).

A solution of the above ethyl 2-ethoxycarbonyl-9-oxa-12-thiatetradecanoate (2 g, 5.8 mmol) in 20% NaOH (10 mL) was refluxed for 6 h. The solution was acidified with HCl (pH 2), and extracted with ethyl acetate (120 mL). The organic phase was washed with water (2×30 mL), brine (30 mL) and dried (Na$_2$SO$_4$). After evaporation of the solvent, the resulting product was heated on an oil bath at 180° C. to 200° C. for 15 min. The crude product was purified by Kugelrohr distillation to afford the title compound, 9-oxa-12-thiatetradecanoic acid (1.4 g, 98%); bp 121° C.-125° C./0.005 torr; IR(neat):3020 (broad) and 1730 cm$^{-1}$; $^1$NMR: 1.27 (3H, t, J=7.7 Hz), 1.34 (6H, m), 1.53-1.68 (4H, m), 2.36 (2H, t, J=7.1 Hz), 2.58 (2H, q, J=7.7 Hz), 2.71 (2H, t, J=7 Hz), 3.45 (2H, t, J=6.8 Hz), 3.59 (2H, t, J=7 Hz), and 10.6 ppm (1H, br s); Found: C, 58.11, H, 9.8%. Calcd for C$_{12}$H$_{24}$SO$_3$: C, 58.03, H, 9.74%.

EXAMPLE 8

Ethyl 9-thia-12-oxatetradecanoater

NaH (0.39g, 9.6 mmol) was washed with hexane and then suspended in dry THF (45 mL). 5-Ethoxypentane-1-thiol (8.7 mmol) in THF (8 mL) was added and stirred for 1 h at room temperature. Ethyl 8-iodooctanoate (2.4 g, 8.7 mmol) in THF (7 mL) was added and the mixture was refluxed for 6 h. After evaporation of the solvent, the residue was taken into ethyl acetate (150 mL). The organic phase was washed with water (2 ×50 mL), brine (50 mL), and dried ($Na_2SO_4$). The crude product was purified by column chromatography on silica gel with ethyl acetate:hexane (1:5) and subsequent Kugelrohr distillation to give the title compound, ethyl 9-thia-12-oxatetradecanoate; yield 52%; bp 118° C.-120° C./0.15 torr; NMR: 1.2 (3H, t, J=7 Hz), 1.25 (3H, t, J=7 Hz), 1.2-1.8 (10 H, m), 2.28 (2H, t, J=6.5 Hz), 2.55 (2H, t, J=7 Hz), 2.67 (2H, t, J=7 Hz), 3.44 (2H, t, J=7 Hz), 3.66 (2H, t, J=7 Hz), and 4.1 ppm (2H, q, J=7 Hz).

9-Thia-12-oxatetradecanoic Acid

NaOH (1M, 24 mL, 24 mmol) was added to a solution of the above ethyl 9-thia-12-oxatetradecanoate. (6.8 mmol) in MeOH (20 mL). After stirring for 7 h, the reaction mixture was acidified with 10% HCl (pH 1) and extracted with ethyl acetate (2×100 mL). The organic phase was washed with water (50 mL), brine (50 mL), and dried ($Na_2SO_4$). The crude product was recrystallized from hexane to afford the title compound, 9-thia-12-oxatetradecanoic acid; yield 92%; bp 134° C.-136° C./0.005 torr; IR (neat): 3000 (broad) and 1735 $cm^{-1}$ NMR: 1.23 (3H, t, J=7.2 Hz), 1.28-1.46 (6H, m), 1.53-1.68 (4H, m), 2.35 (2H, t, J=7.3 Hz), 2.54 (2H, t, J=7.1 Hz), 2.70 (2H, t, J=7.1 Hz), 3.52 (2H, q, J=7.2 Hz), 3.60 (2H, t, J=6.9 Hz), and 8.85 ppm (1H, br s); Found: C, 57.96, H, 9.77%. Calcd for $C_{12}H_{24}SO_3$: C, 58.03, H, 9.74%.

EXAMPLE 9

Ethyl 6-thia-12-oxatetradecanoate

NaH (0.39 g, 9.6 mmol) was washed with hexane and then suspended in dry THF (45 mL). 2-Ethoxyethane-1-thiol (8.7 mmol) in the THF (8 mL) was added and stirred for 1 h at room temperature. Ethyl 8-iodooctanoate (8.7 mmol) in THF (7 ml) was added and the mixture was refluxed for 6 h. After evaporation of the solvent, the residue was taken into ethyl acetate (150 mL). The organic phase was washed with water (2×50 mL), brine (50 mL), and dried ($Na_2SO_4$). The crude product was purified by column chromatography on silica gel with ethyl acetate:hexane (1:5) and subsequent Kugelrohr distillation to give the title compound, ethyl 6-thia-12-oxatetradecanoate; yield 81%; bp 116° C.-120° C./0.1 torr; IR(neat): $1745^{-1}$; NMR: 1.18 (3H, t, J=7 Hz), 1.25 (3H, t, J=7 Hz), 1.45-1.9 (10H, m), 2.2-2.7 (6H, m), 3.45 (2H, q, J=7 Hz), 3.39 (2H, t, J=6 Hz), and 4.12 ppm (2H, q, J=7 Hz).

6-Thia-12-oxatetradecanoic Acid

NaOH (1M, 24 mL, 24 mmol) was added to a solution of the above ethyl-6-thia-12-oxatetradecanoate, (6.8 mmol) in MeOH (20 mL). After stirring for 7 h, the reaction mixture was acidified with 10% HCl (pH 1) and extracted with ethyl acetate (2×100 mL). The organic phase was washed with water (50 mL), brine (50 mL), and dried ($Na_2SO_4$). The crude product was recrystallized from hexane to afford the title compound, 6-thia-12-oxatetradecanoic acid; yield 82%; bp 144° C.-146° C./0.01 torr; IR(neat): 3000 (broad) and 1730 $cm^{-1}$; NMR: 1.23 (3H, t, J=7.3 Hz), 1.46 (2H, quint, J=6.9 Hz), 1.55-1.69 (6H, m), 1.74 (2H, quint, J=7.3 Hz), 2.37 (2H, t, J=7.6 Hz), 2.51 (2H, t, J=7 Hz), 2.53 (2H, t, J=7 Hz)m 3,42 (2H, t, J=6.9 Hz), 3.48 (2H, q, J=7.3 Hz), and 10.6 ppm (1H, br s); Found: C, 58.07, H, 9.78%. Calcd for $C_{13}H_{26}SO_2$: C, 58.03, H, 9.74%.

EXAMPLE 10

Compounds prepared in the foregoing illustrative specific examples were analyzed in a conventional in vitro yeast N-myristoyltransferase (NMT) assay as published by Heuckeroth et al., Proc. Nat'l. Acad. Sci. USA 85, 8795-8799 (1988). In this assay, the test compounds were first converted to their respective fatty acyl CoA derivatives and then tested as substrates for the yeast NMT.

The assay conditions [essentially the same as those reported by Towler and Glaser, Proc. Natl. Acad. Sci. USA 83, 2812-2816 (1986)]were as follows:

1. Ligase reaction: 3.3 μmoles fatty acid, 5 mM ATP and 1 mM CoA were incubated with 15-150 milliunits of CoA ligase (1 unit/ml in 50 mM HEPES, pH 7.3) in a buffer composed of 10 mM TRIS HCl, pH 7.4, 1 mM dithiothreitol, 5 mM $MgCl_2$ and 0.1 mM EGTA, in a total volume of 50 μl for 25 minutes at 30° C.

2. NMT assay: 50 μl of the CoA ligase mixture was added to a 50 μl solution of 90 μM peptide (GSAA-SARR-$NH_2$) in a buffer composed of 10 mM TRIS HCl, pH 7.4, 1 mM dithiothreitol, 0.01 mM EGTA and aprotinin (10 μg/ml). 0.4 Unit of yeast N-myristoyltransferase was then added and the reaction mixture was incubated at 30° C. for 10 minutes. The peptide was radiolabeled with tritium in alanine in position 3. The reaction was quenched with 120 μl of TCA-MEOH and 75 μl was injected on a reverse phase C18 HPLC column and eluted with a linear gradient of 0%-100% acetonitrile over 100 minutes (both water and acetonitrile containing 0.1% trifluoroacetic acid). Radioactivity was assessed with an on line radiomatic detector corrected for quenching.

The amount of radioactivity was determined for each diheteroatom-substituted fatty acyl peptide product and then was normalized to the amount of myristoyl peptide produced in an assay run in parallel.

The activity of each fatty acid analog was thus expressed as a percentage of the activity exhibited by unsubstituted myristate (control) and recorded in the following Table 1.

TABLE I

Substrate Activity of Diheteroatom Fatty Acid Analogs

| Test Compound | | Myristate Analog | Activity (% of Myristate) |
|---|---|---|---|
| A. | Example 2 | 6,12-dithia | 95% |
| B. | Example 5 | 6,12-dioxa | 4% |
| D. | Example 3 | 7,10-dioxa | 6% |
| E. | Example 4 | 9,12-dioxa | 11% |
| G. | Example 7 | 9-oxa-12-thia | 37% |
| H. | Example 8 | 9-thia-12-oxa | 61% |
| I. | Example 6 | 10,13-dioxa | 7% |
| J. | Example 9 | 6-thia-12-oxa | 38% |

Various other examples will be apparent to the person skilled in the art after reading the present disclosure without departing from the spirit and scope of the invention. All such other examples are included within the scope of the appended claims.

What is claimed is:

1. A diheteroatom-substituted fatty acid analog compound having activity as a substrate for myristoylating enzymes selected from the group consisting of $C_{13}$ or $C_{14}$ fatty acids or alkyl esters thereof in which two methylene groups normally in carbon positions from 3 to 13 are replaced by oxygen and/or sulfur and in which said oxygen or sulfur atoms are separated by at least one methylene group.

2. A compound of claim 1 in which two methylene groups are replaced by oxygen.

3. A compound of claim 1 in which two methylene groups are replaced by sulfur.

4. A compound of claim 1 in which one methylene group is replaced with oxygen and another methylene group is replaced by sulfur.

5. A compound of claim 1 in which the fatty acid is a saturated $C_{13}$ or $C_{14}$ fatty acid.

6. A compound of claim 1 in which the heteroatoms are separated by from 2 to 5 methylene groups.

7. 6,12-Dithiatetradecanoic acid or $CH_3CH_2S(CH_2)_5S(CH_2)_4COOH$.

8. 6,12-Dioxatetradecanoic acid or $C_3CH_2O(CH_2)_5O(CH_2)_4COOH$.

9. 7,10-Dioxatetradecanoic acid or $CH_3(CH_2)_3O(CH_2)_2O(CH_2)_5COOH$.

10. 9,12-Dioxatetradecanoic acid or $CH_3CH_2O(CH_2)_2O(CH_2)_7COOH$.

11. 9-Oxa,12-thiatetradecanoic acid or $CH_3CH_2S(CH_2)_2O(CH_2)_7COOH$.

12. 12-Oxa,9-thiatetradecanoic acid or $CH_3CH_2O(CH_2)_2S(CH_2)_7COOH$.

13. 10,13-Dioxatetradecanoic acid or $CH_3O(CH_2)_2O(CH_2)_8COOH$.

14. 12-Oxa-6-thiatetradecanoic acid or $CH_3CH_2O(CH_2)_5S(CH_2)_4COOH$.

* * * * *

UNITED STATES PATENT AND TRADEMARK OFFICE
CERTIFICATE OF CORRECTION

PATENT NO. : 5,082,967

DATED : January 21, 1992

INVENTOR(S) : R. O. Heuckeroth, S. P. Adams, J. I. Gordon and G. W. Gokel

It is certified that error appears in the above-identified patent and that said Letters Patent is hereby corrected as shown below:

At col. 1, line 58 "198" should read --1988--. At col. 2, line 1 "inhibits" should read -- inhibitors--. At col. 2, line 66 "$CH_3H_2O(CH_2)_2S(CH_2)_7COOH$" should read --$CH_3CH_2O(CH_2)_2S(CH_2)_7COOH$--. At col. 3, after "e.g." insert --myristic acid. Thus, compound A can also be--. At col. 9, line 2, "oxatetradeonoater" should read --oxatetradecanoate--.

Signed and Sealed this

Twenty-second Day of June, 1993

Attest:

MICHAEL K. KIRK

Attesting Officer

Acting Commissioner of Patents and Trademarks